United States Patent [19]

Slayton

[11] Patent Number: 5,291,893
[45] Date of Patent: Mar. 8, 1994

[54] ENDO-LUMINAL ULTRASONIC INSTRUMENT AND METHOD FOR ITS USE

[75] Inventor: Michael H. Slayton, Tempe, Ariz.

[73] Assignee: Acoustic Imaging Technologies Corporation, Phoenix, Ariz.

[21] Appl. No.: 959,150

[22] Filed: Oct. 9, 1992

[51] Int. Cl.⁵ .............................................. A61B 8/12
[52] U.S. Cl. .......................... 128/662.06; 128/660.08; 128/662.03
[58] Field of Search ........................ 128/660.05, 660.08, 128/661.01, 662.03, 662.06

[56] References Cited

U.S. PATENT DOCUMENTS

| | | | |
|---|---|---|---|
| 4,917,097 | 4/1990 | Proudian et al. | 128/661.01 |
| 5,010,886 | 4/1991 | Passafaro et al. | 128/662.06 |
| 5,085,221 | 2/1992 | Ingebrigtsen et al. | 128/662.06 |
| 5,131,396 | 7/1992 | Ishiguro et al. | 128/662.06 |
| 5,186,177 | 2/1993 | O'Donnell et al. | 128/661.01 |

Primary Examiner—William E. Kamm
Assistant Examiner—George Manuel
Attorney, Agent, or Firm—Christie, Parker & Hale

[57] ABSTRACT

An endo-luminal ultrasonic instrument has a motor with a rotatable drive shaft that oscillates back and forth. A flexible catheter sheath is coupled at one end to the motor to oscillate with the drive shaft. The sheath has an axis about which it oscillates and a diameter sized to fit inside a human blood vessel or other body lumen. An ultrasonic transducer is attached to the other end of the sheath to oscillate therewith. The transducer has an array of individually operable elements arranged parallel to the axis to form a rotatable beam perpendicular to the axis. Electronics near the motor operates the transducer elements. Wiring, passing through the catheter sheath connects electrically the transducer elements and the electronics. The electronics includes electronic beam focusing to enhance the axial resolution of the instrument.

25 Claims, 3 Drawing Sheets

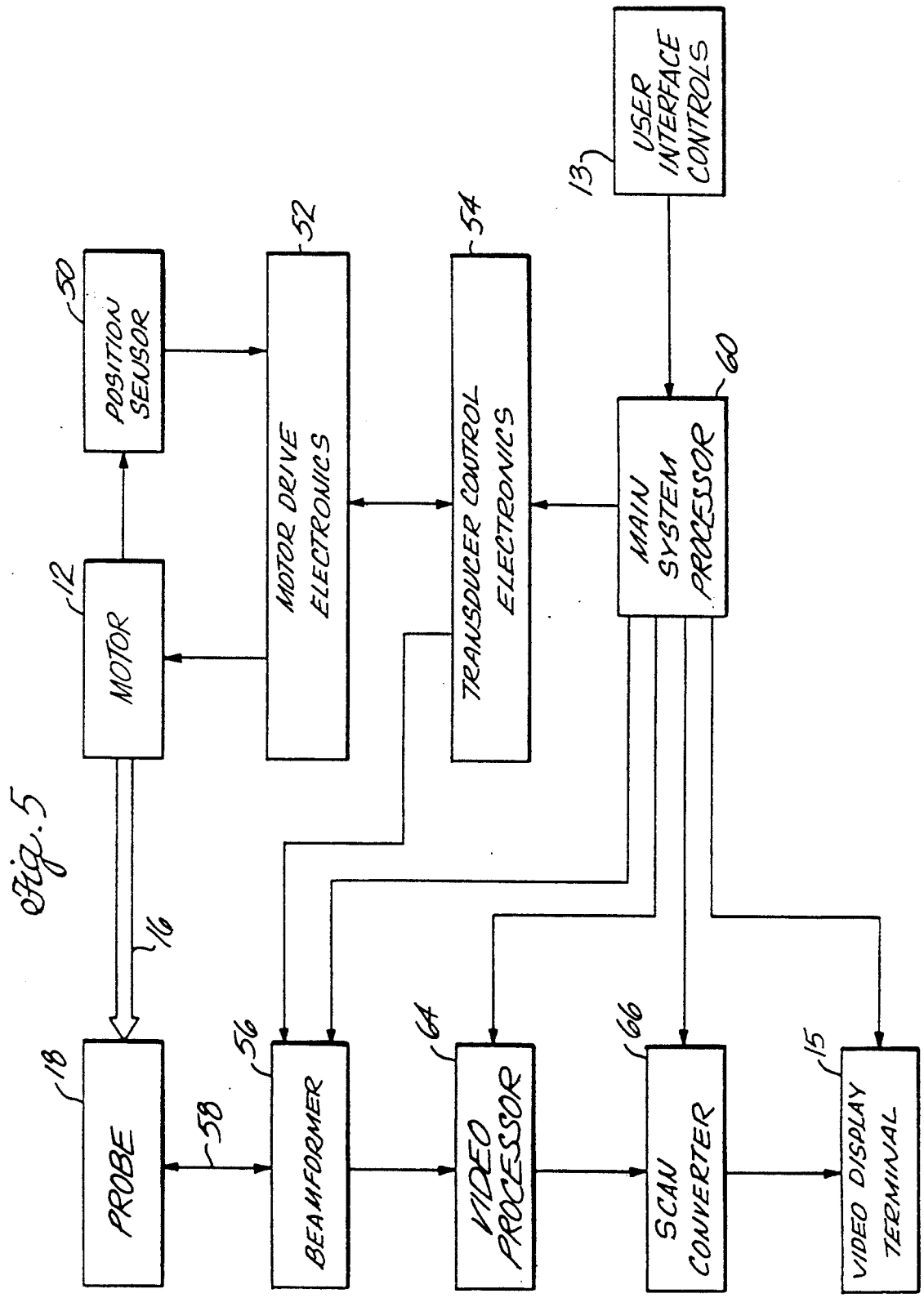

ENDO-LUMINAL ULTRASONIC INSTRUMENT AND METHOD FOR ITS USE

BACKGROUND OF THE INVENTION

This invention relates to medical ultrasound imaging, and more particularly, to an endo-luminal ultrasonic instrument and method for its use.

One type of endo-luminal ultrasonic instrument has a single rotating ultrasonic transducer element or ultrasonic reflector at the end of a flexible stationary catheter. The transducer element or reflector rotates with respect to the catheter to perform a B-scan in a plane perpendicular to the axis of the catheter.

Another type of endo-luminal ultrasonic instrument has a plurality of stationary ultrasonic transducer elements arranged around the circumference of the end of a flexible stationary catheter. The transducer elements are sequentially actuated in groups to perform a B-scan in a single plane perpendicular to the axis of the catheter. This type of instrument is disclosed in U.S. Pat. No. 3,938,505 to Bom. Being confined to a single plane perpendicular to the catheter axis, both of the described types of instruments do not exhibit good longitudinal, i.e., axial resolution.

Herres U.S. Pat. No. 5,070,879 discloses a hand-held transrectal ultrasonic imaging instrument incorporated in a rigid longitudinal housing. Inside the housing, an array of ultrasonic transducer elements is axially arranged for oscillation about the longitudinal axis.

SUMMARY OF THE INVENTION

The invention incorporates the principles of the above-identified Herres patent in an endo-luminal ultrasonic instrument. Specifically, in one aspect of the invention, an endo-luminal ultrasonic instrument has a motor with a rotatable drive shaft that oscillates back and forth. A flexible catheter sheath is coupled at one end to the motor to oscillate with the drive shaft. The sheath has an axis about which it oscillates and a diameter sized to fit inside a human blood vessel. An ultrasonic transducer is attached to the other end of the sheath to oscillate therewith. The transducer has an array of individually operable elements arranged parallel to the axis to form a rotatable beam perpendicular to the axis. Electronics near the motor operates the transducer elements. Wiring, passing through the catheter sheath connects electrically the transducer elements and the electronics. In the preferred embodiment, electronics operate the transducers successively to perform B-scans at different angles about the axis, and the wiring comprises a plurality of wires individually connecting the elements to the electronics. The electronics includes electronic beam focusing to enhance the axial resolution of the instrument.

Another aspect of the invention is a method for ultrasonically imaging human body parts endo-luminally. An array of longitudinally arranged ultrasonic transducer elements and a flexible catheter sheath are inserted into a blood vessel or other fluid bearing lumen of a human body being imaged. Wiring from the array is directed through the sheath to electronic circuitry outside the human body for controlling operation of the array. The sheath and the array are oscillated together in the blood vessel or other lumen during operation of the array to couple ultrasonic pulses through the fluid to the surrounding body structure. The echoes are processed and displayed to permit examination of the body structure surrounding the lumen.

BRIEF DESCRIPTION OF THE DRAWINGS

The features of specific embodiments of the best mode contemplated of carrying out the invention are illustrated in the drawings, in which:

FIG. 5 is a schematic block diagram of the entire ultrasonic imaging system, in which the ultrasonic transducer and catheter are incorporated.

DETAILED DESCRIPTION OF THE SPECIFIC EMBODIMENTS

Figure 1:
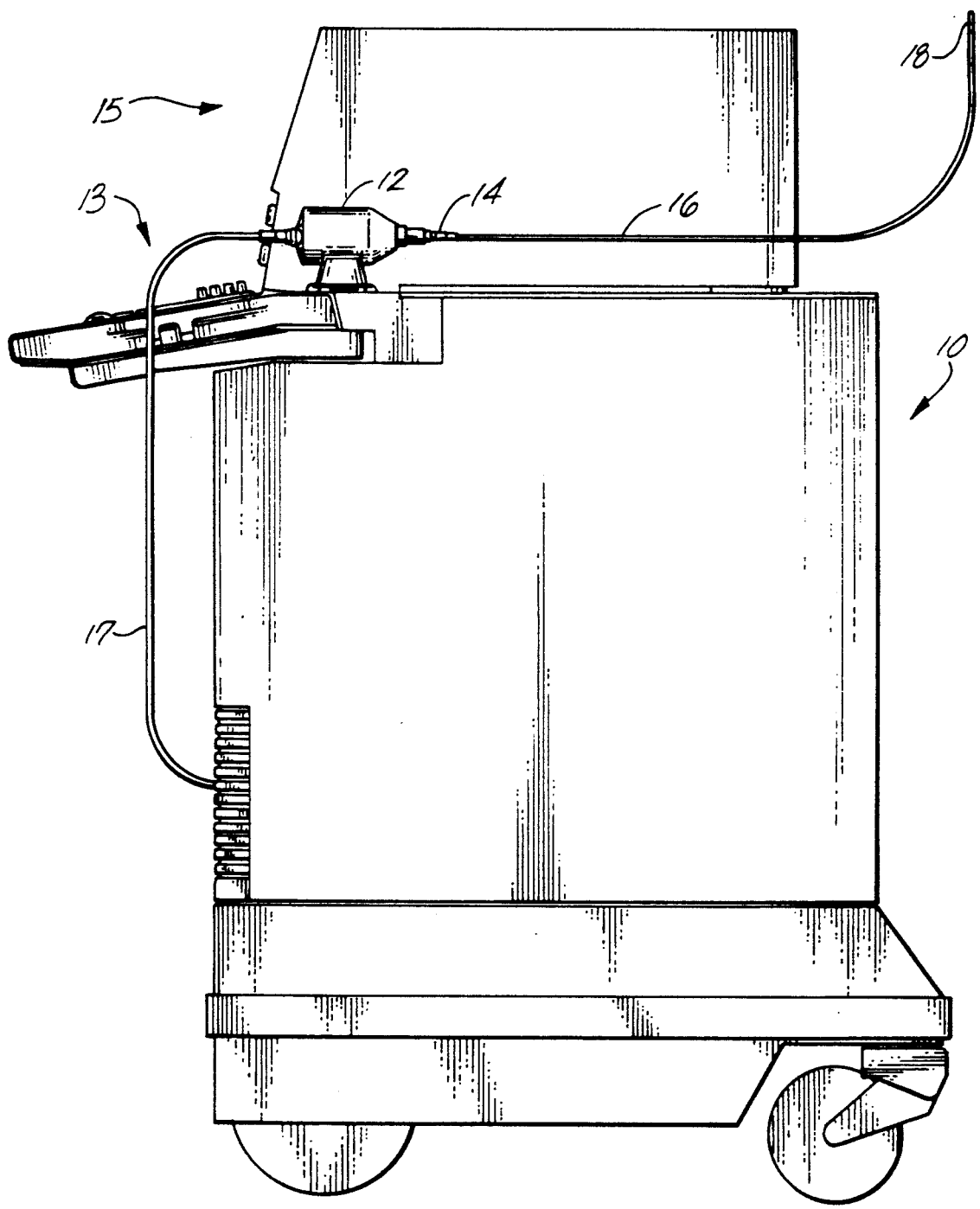
FIG. 1 is a side elevation view of a medical ultrasound imaging system including an endo-luminal instrument that incorporates principles of the invention.

In FIG. 1, a medical ultrasound imaging system has a console 10. User interface controls 11 are located on a sloped control panel on the left side of console 10 as viewed in FIG. 1. A motor 12 is mounted on console 10 near user interface controls 11. Motor 12 has a hollow rotatable drive shaft 14 that oscillates, preferably through an angle of 360°. A video display terminal 15 is located in front of user interface controls 11. The near end of a flexible catheter sheath 16 is attached to drive shaft 14 to oscillate therewith. The diameter of sheath 16 is sized to fit inside a human blood vessel, typically of the order of 2.25 mm, or other fluid bearing lumen such as the urethra. An ultrasonic transducer probe is attached to the distal end of catheter sheath 16. A signal cable 17 is electrically connected from motor 12 to the interior of console 10.

Figure 2:
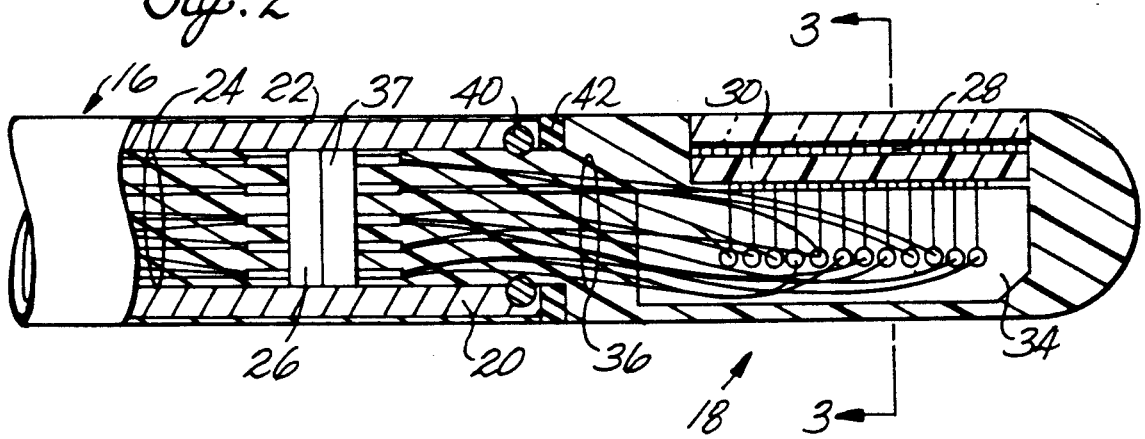
FIG. 2 is a side sectional view of the end of the catheter of FIG. 1 showing the ultrasonic transducer and the electrical connections.
Figure 3:
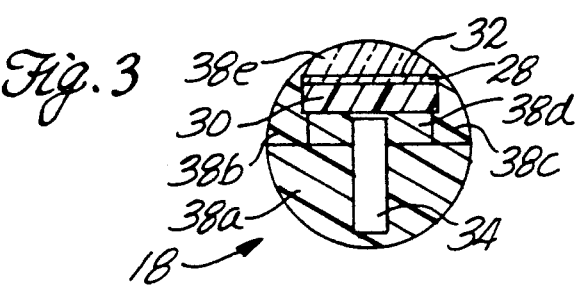
FIG. 3 is a sectional view through the ultrasonic transducer taken through plane 3—3 in FIG. 2.
Figure 4:
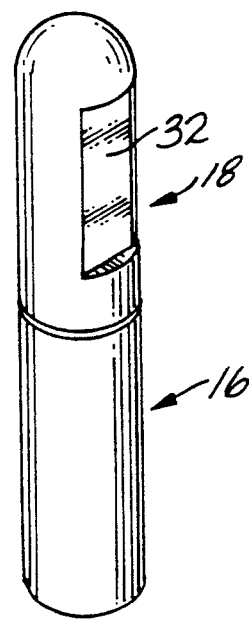
FIG. 4 is a perspective view of the end of the catheter and the ultrasonic transducer.

As shown in detail in FIGS. 2 to 4, ultrasonic transducer probe 18 is attached to the distal end of sheath 16. Preferably, sheath 16 comprises a hollow tube 20 made of a corrosion resistant material, such as stainless steel, having an outer coating 22 made from a low friction material, such as Teflon. A commercially available catheter could be used. A plurality of wires 24 pass through sheath 16 from its distal end to motor 12 at console 10. Wires 24 terminate at a male connector 26.

Probe 18 comprises an array of electrically separate ultrasonic elements 28 made of a piezoelectric ceramic material. A slab 30 of backing material is bonded to the rear of array 28 leaving a flat active face 32 for emission of ultrasonic energy. A printed circuit board 34 is disposed behind backing slab 30. Printed circuit board 34 has circuitry that is connected to individual elements 28. A slot could be formed in backing slab 30 for this purpose. Wires 36 connect terminal pads on circuit board 34 to a female connector 37, which mates with connector 26. Probe 18 has a housing cast as parts 38a, 38b, 38c, 38d and 38e in a cylindrical shape rounded at its distal end and stepped down at its sheath connecting end. The cast parts are bonded together to form the probe housing as shown. Housing parts 38a, 38b, 38c and 38d are made from a nonreactive material, such as urethane and housing part 38e is made from an ultrasonic energy transmissive material. Part 38e is optional; face 32 could serve as an exterior surface of probe 18. Connector 37 is disposed at the stepped down end of the housing, which fits inside the hollow distal end of sheath 16. An O-ring retainer 40 and a compression seal 42 secure and seal the interface between probe 18 and sheath 16. In a typical embodiment, the active area of array 28 is 3.8 mm by 1.5 mm and the number of elements is 24 plus 3 guard elements at each end.

Sheath 16 and probe 18 would typically be positioned in the lumen using well known guide wire techniques. The guide wire would lead the distal end of sheath 16 and probe 18 into the lumen. The guide wire could pass through the hollow interior of sheath 16 and a hole (not shown) formed in the housing of probe 18 or sheath 16 and probe 18 could pass along side of the guide wire.

Sheath 16 and probe 18 are usually smaller in diameter than the lumen. Therefore, provision is preferably made to anchor the distal end of sheath 16 and probe 18 to keep it from moving back and forth or axially in the lumen during examination of the body structure. By way of example, a balloon at the distal end of sheath 16 could be inflated after the sheath is in place in the lumen. The balloon could be fixed to sheath 16 to rotate therewith or could be attached to sheath 16 by ball bearings to remain stationary as sheath 16 rotates. Alternatively, the distal end of sheath 16 could be anchored by a sheath that fills the space between the distal end of sheath 16 and the lumen wall.

At the distal end of sheath 16, wires 24 and 36 oscillate with sheath 16 and probe 18. At the near end of sheath 16, however, wires 24 are anchored to the stationary housing of motor 12. Thus, wires 24 twist back and forth as motor 12 oscillates. Sheath 16 is so long that the twist per unit length is slight. Typically, sheath 16 is 50 to 100 cm. or more in length. To make the electrical connection with cable 17, wires 24 could pass through hollow drive shaft 14 and the interior of motor 12.

FIG. 5 is a block diagram of the entire ultrasound imaging system, including motor 12, sheath 16, and probe 18. As illustrated, motor 12 is coupled by sheath 16 to probe 18 and also coupled to a position sensor 50. Motor drive electronics 52 controls the operation of motor 12 responsive to position sensor 50 and transducer control electronics 54. Probe 18 is electrically connected to a beamformer 56 by wires 36, connectors 26 and 38, wires 24 and signal cable 17, which are together represented in FIG. 5 by an electrical connection 58. Beamformer 56 serves to focus the transmitted and-/or received ultrasonic energy, preferably by means of introducing electrical delays into the signal paths for the array elements. Beamformer 56 is operated responsive to transducer control electronics 54 and a main system controller 60, which is responsive to user interface controls 13. The transmission pulse generating signals for probe 18 are produced in transducer control electronics 54 and are coupled therefrom through beamformer 56 and electrical connection 58 to probe 18. The electrical echo signals produced by probe 18 are coupled through electrical connection 58 and beamformer 56 to a video processor 64. Video processor 64 processes the high frequency electrical signals to form image signals, which are coupled to a scan converter 66. The image signals are stored and composed in scan converter 66 for application to video display terminal 15. The main system controller 60 regulates the operation of video processor 64, scan converter 66, and video display terminal 70 in well-known fashion. Reference is made to U.S. Pat. No. 5,140,558, the disclosure which is incorporated herein fully by reference for a further description of the apparatus shown in FIG. 5. Position sensor 50, motor drive electronics 52, transducer control electronics 54, beamformer 56, video processor 64, and scan converter 68 are housed inside console 10 (FIG. 1).

As disclosed in Herres U.S. Pat. No. 5,070,879 (the disclosure of which is incorporated herein by reference), motor 12 can be operated so its drive shaft 14 oscillates continuously or intermittently. Typically, the depth of field of the instrument is of the order of 3 to 4 cm. and the angular velocity for motor 12 is about one RPM. In any case, its operation is synchronized to the operation of video display terminal 70 by main system processor 60. Transducer elements 28 could be operated successively to execute B-scans in planes parallel to the axis of probe 18 at different angles around axis 18 or in unison to execute a single B-scan in a plane perpendicular to the axis of probe 18 as probe 18 oscillates. If transducer elements 28 are operated successively while probe 18 oscillates continuously, the three dimensional data that is acquired could be displayed in a three dimensional format.

The described embodiment of the invention is only considered to be preferred and illustrative of the inventive concept; the scope of the invention is not to be restricted to such embodiments. Various and numerous other arrangements may be devised by one skilled in the art without departing from the spirit and scope of this invention. For example, sheath 16 could be disposed inside of a non-rotating outer tube, rather than directly inside the blood vessel, all be it at the cost of a larger tube diameter.

What is claimed is:

1. An endo-luminal ultrasonic instrument comprising:
   a motor having a fixed housing and a rotatable drive shaft that oscillates relative to the housing;
   a flexible catheter sheath coupled at one end to the motor to oscillate with the drive shaft, the sheath having an axis about which it oscillates;
   an ultrasonic transducer coupled to the other end of the sheath to oscillate therewith;
   electronic means near the motor for operating the transducer;
   wiring passing through the sheath to connect electrically the transducer and the electronic means;
   means for attaching one end of the wiring to the transducer to oscillate therewith; and
   means for attaching the other end of the wiring to the motor housing so the wiring twists as the transducer oscillates.

2. The instrument of claim 1, in which the transducer has an array of individually operable elements arranged parallel to the axis to form a rotatable beam perpendicular to the axis.

3. The instrument of claim 2, in which the electronic means operates the transducer elements successively to perform B-scans and the wiring comprises a plurality of wires individually connecting the elements to the electronic means.

4. The instrument of claim 3, in which the electronic means includes means for focusing the beam.

5. The instrument of claim 4, in which the sheath has an outer surface coated with a low friction material.

6. The instrument of claim 4, in which the diameter of the sheath is of the order of 2.25 mm.

7. The instrument of claim 3, in which the sheath has an outer surface coated with a low friction material.

8. The instrument of claim 3, in which the diameter of the sheath is of the order of 2.25 mm.

9. The instrument of claim 2, in which the sheath has an outer surface coated with a low friction material.

10. The instrument of claim 2, in which the diameter of the sheath is of the order of 2.25 mm.

11. The instrument of claim 1, in which the sheath has an outer surface coated with a low friction material.

12. The instrument of claim 11, in which the diameter of the sheath is of the order of 2.25 mm.

13. The instrument of claim 1, in which the diameter of the sheath is of the order of 2.25 mm.

14. The instrument of claim 1, in which the diameter of the sheath is sized to fit inside a blood vessel.

15. The instrument of claim 1, in which the electronic means includes means for focusing the beam.

16. The instrument of claim 1, in which the diameter of the sheath is of the order of 2.25 mm.

17. A method for ultrasonically imaging parts of a human body comprising the steps of:
   inserting into a fluid bearing lumen of the human body being imaged an array of longitudinally arranged ultrasonic elements attached to one end of a flexible catheter sheath with an outer surface that creates low friction;
   directing wiring from the array through the sheath to electronic circuitry outside the human body for controlling operation of the array, one end of the wiring being connected to the array and the other end of the wiring being connected to the electronic circuitry;
   oscillating the sheath and the array together in the lumen during operation of the array to acquire ultrasonic data about the structure of the body around the blood vessel;
   anchoring the other end of the wiring so the one end of the wiring twists as the array oscillates; and
   processing and displaying the acquired data.

18. The method of claim 17, additionally comprising the step of firing the ultrasonic elements successively as the array oscillates to form B-scan images along the array.

19. The method of claim 17, additionally comprising the step of focusing the array.

20. The method of claim 17, additionally comprising the step of firing the ultrasonic elements in unison as the array oscillates to form a B-scan image transverse to the array.

21. The method of claim 17, additionally comprising the step of firing the ultrasonic elements successively as the array oscillates to form three dimensional images around the array.

22. The method of claim 21, additionally comprising the step of focusing the three dimensional images.

23. The method of claim 17, additionally comprising after the inserting step the step of actuating anchoring means to anchor the one end of the sheath to the lumen against axial movement.

24. The method of claim 23, in which the actuating step anchors the anchoring means to rotate with the one end of the sheath relative to the lumen.

25. The method of claim 23, in which the actuating step anchors the anchoring means to be stationary relative to the lumen, a rotatable relative to the sheath.

* * * * *